United States Patent [19]

Stephens, Jr.

[11] 4,134,907

[45] Jan. 16, 1979

[54] PROCESS FOR ENHANCING THE FUEL VALUE OF LOW BTU GAS

[75] Inventor: Frank M. Stephens, Jr., Lakewood, Colo.

[73] Assignee: Hazen Research, Inc., Golden, Colo.

[21] Appl. No.: 817,576

[22] Filed: Jul. 21, 1977

[51] Int. Cl.$^2$ ................................................ C07C 1/04
[52] U.S. Cl. ......................... 260/449.6 M; 48/197 R; 260/676 R
[58] Field of Search .................. 260/449 M, 449.6 M, 260/449.6 R, 676; 48/197

[56] References Cited

U.S. PATENT DOCUMENTS

| 2,409,235 | 10/1946 | Atwell | 260/449.6 |
|---|---|---|---|
| 2,537,496 | 1/1951 | Watson | 260/449.6 |
| 2,562,802 | 7/1951 | Mayer | 260/449.6 |
| 2,589,925 | 3/1952 | Cain et al. | 260/449.6 |
| 2,601,121 | 6/1952 | Mattox | 260/449.6 |
| 2,686,819 | 8/1954 | Johnson | 260/449 M |
| 2,694,624 | 11/1954 | Sweetser | 260/449 M |
| 2,819,283 | 1/1958 | Montgomery et al. | 260/449.6 |
| 4,005,996 | 2/1977 | Hausberger | 260/449 M |

Primary Examiner—Howard T. Mars
Attorney, Agent, or Firm—Sheridan, Ross, Fields & McIntosh

[57] ABSTRACT

A process for increasing the fuel value of a gas mixture of carbon monoxide and hydrogen by converting part of the hydrogen and part of the carbon in the carbon monoxide of the gas mixture to methane, which comprises continuously introducing the gas mixture into a fluid bed in the presence of iron under conditions of pressure and temperature which promote the reduction of carbon monoxide to carbon, the formation of iron carbide from the iron and carbon, and the formation of methane and iron from iron carbide and hydrogen, and continuously removing from the fluid bed a methane enriched gas mixture including carbon monoxide and hydrogen having a substantially increased fuel value over the gas mixture introduced into the fluid bed.

7 Claims, 3 Drawing Figures

Fe-O-H-C STABILITY DIAGRAM AT 1160°F (900°K)

Fe-O-H-C STABILITY DIAGRAM AT 1070°F (850°K)

Fe-O-H-C STABILITY DIAGRAM AT 1250°F (950°K)

PROCESS FOR ENHANCING THE FUEL VALUE OF LOW BTU GAS

BACKGROUND OF THE INVENTION

The need to use the extensive coal resources in this country as a source of fuel gas is now quite evident in view of the rapid depletion of other sources. Accordingly, it has become essential to develop processes for the economic production of fuel gas for industrial uses from coal.

Atmospheric coal gasification processes are well known and well developed. Typical of these proven processes are the Koppers-Totzek, Winkler, Wellman-Galusha, Woodall-Duckman, and others. The gas produced from these gasification processes is a low Btu gas comprising a mixture of carbon monoxide and hydrogen. This gas mixture has a low fuel value of about 300 Btu/ft$^3$ or less, on the average, which is too low for most industrial uses.

The fuel value of the gas produced by the atmospheric coal gasification processes can be enhanced with the use of high temperatures and pressures, sometimes accompanied by the use of oxygen and/or catalysts, to make the hydrogen and carbon monoxide present react to produce methane. Methane has a heat of combustion of 1013 Btu/ft$^3$, whereas carbon monoxide and hydrogen have Btu's of about 322 and 325, respectively. The chief disadvantage, of course, of these procedures for enhancing the fuel value of the low Btu gas is the expense involved. The expense is so great that low Btu gas enhanced in this manner is not competitive with other fuels available for industrial uses.

So-called intermediate Btu gas is suitable for industrial uses, this gas having a Btu value of 450 Btu/ft$^3$ or more. It will burn well in existing gas burner equipment in power plants and other industrial applications with only minor modification in the burner head. The Btu value is high enough so that its use does not result in loss of boiler efficiency and, further, this gas can be economically piped moderate distances, which is not true for low Btu gas.

Accordingly, it is an object of this invention to provide a relatively inexpensive process for enhancing the fuel value of the low Btu gas produced by coal gasification processes.

SUMMARY OF THE INVENTION

A process for increasing the fuel value of a gas mixture of carbon monoxide and hydrogen by converting part of the hydrogen, and part of the carbon in the carbon monoxide of the gas mixture to methane, which comprises continuously introducing the gas mixture into a fluid bed in a single reaction zone in the presence of a mixture of iron and iron carbide under conditions of pressure and temperature which promote the reduction of carbon monoxide to carbon along with the formation of iron carbide by the reaction of iron and carbon followed by the formation of methane and iron by the reaction of iron carbide with hydrogen, while continuously removing from the fluid bed a gas mixture including methane, carbon monoxide and hydrogen having a substantially increased fuel value over the gas mixture introduced into the fluid bed. The gas mixture removed has a Btu value of about 600 on the average and is a suitable industrial or utility fuel. If methane alone is required it can be recovered from the gas mixture removed from the fluid bed by conventional procedures.

DESCRIPTION OF PREFERRED EMBODIMENTS

Figure 1:
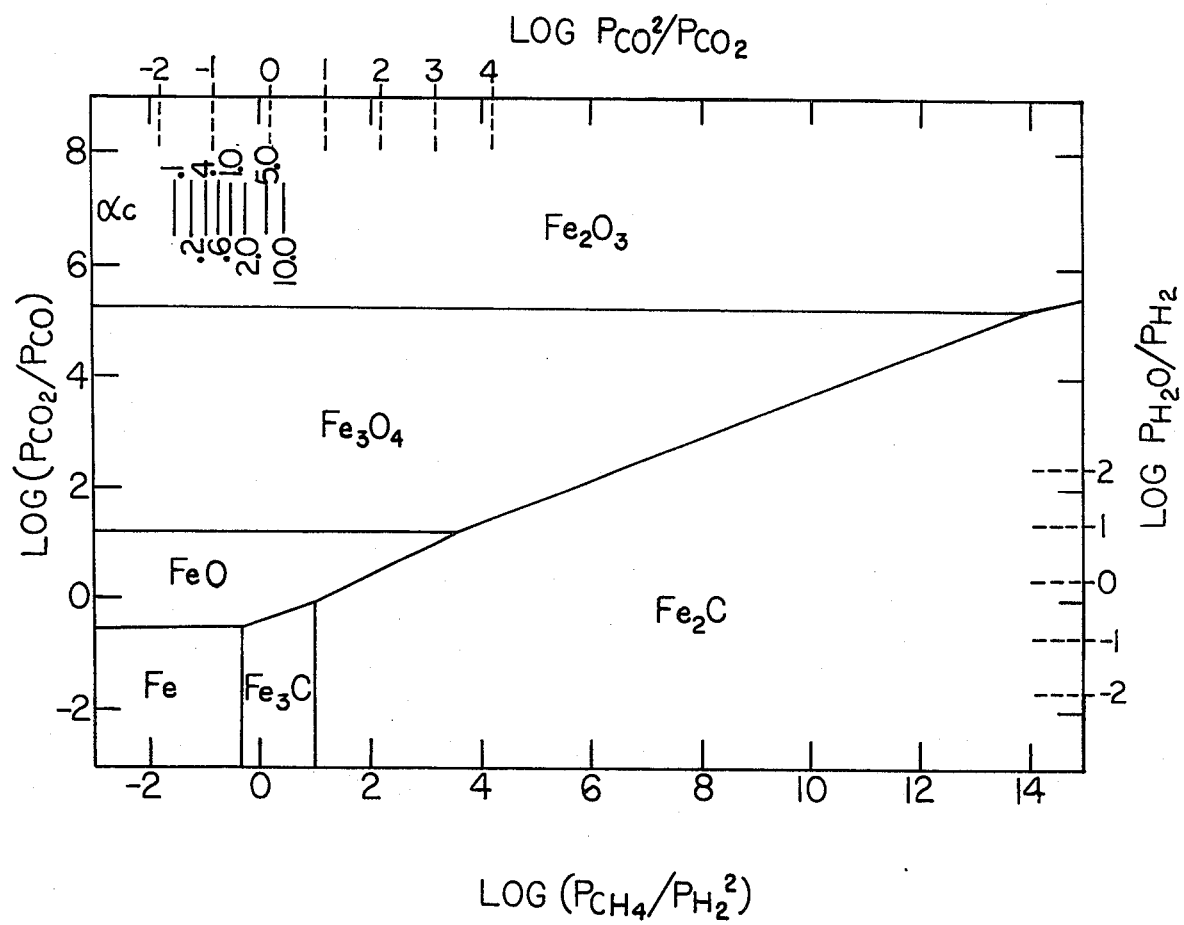
FIGS. 1–3 are stability diagrams indicating the gas phase relationships between iron carbide and the hydrogen-carbon-oxygen system. The symbol $aC$ refers to the activity of carbon in the system. The symbol "P" represents partial pressure. The amounts of gases are essentially directly related to the partial pressures.

The invention is based on establishing and maintaining conditions in a fluid bed which promote the following three reactions:

(1) $CO + H_2 \rightarrow C + H_2O$
(2) $C + 3Fe \rightarrow Fe_3C$
(3) $Fe_3C + 2H_2 \rightarrow 3Fe + CH_4$ These reactions will proceed under atmospheric pressures, although slightly elevated pressures may be preferred.

In the fluid bed reaction, the iron acts as an acceptor of carbon in reaction (2) and as a donor of carbon in reaction (3). It will be noted that iron is reformed or regenerated in reaction (3) and that the iron carbide is reformed or regenerated in reaction (2) so that after the first addition of iron and iron carbide they are always present in the reaction zone without further additions.

Reaction (3) can be made to proceed to the right either by the addition of hydrogen or the removal of methane. Hydrogen and carbon monoxide are being continuously added in reaction (1) and methane, along with the carbon monoxide and hydrogen not converted, is being continuously removed as part of the enriched fuel gas.

The reactions can be made to proceed and controlled by controlling the ratio of the various gases present, that is, the ratio of methane to hydrogen, water to hydrogen, carbon dioxide to carbon monoxide, etc. Charts will be described hereinafter illustrating how control of these ratios results in the reactions proceeding in the required manner.

The fluidized bed reactor referred to herein is of the conventional type in which finely divided feed material on a grate or perforate support is fluidized by upwardly flowing gasses which may include or entirely comprise the reactant gasses. Auxiliary equipment includes heating and temperature control and monitoring equipment, heat exchangers, scrubbers, cyclones, gas cycling equipment and other conventional equipment.

The reactants introduced into the reactor after the initial charge of iron carbide and iron are the low Btu coal gasification gasses containing carbon monoxide and hydrogen.

By proper balancing of the ratios of the hydrogen and carbon bearing materials in accordance with the stability diagrams, it is possible to make the hydrogen serve a reducing function to reduce the carbon monoxide to carbon, and the carbon serve a carburizing function as iron carbide is formed. As stated previously, conditions are established and maintained so that iron serves both a carbon acceptor function and a carbon donor functions. Additionally, reaction conditions are adjusted so that hydrogen performs an additional reducing function in reducing iron carbide to iron and forming methane with the released carbon.

Because of the equilibrium conditions involved in hydrogen-carbon-oxygen gas systems, the required hydrogen-carbon ratios will automatically require that methane be present in the gas system. The quantity of methane present or produced will be a function of carbon to hydrogen ratios, as well as temperature and pressure conditions, and all of these can be controlled.

Figure 2:
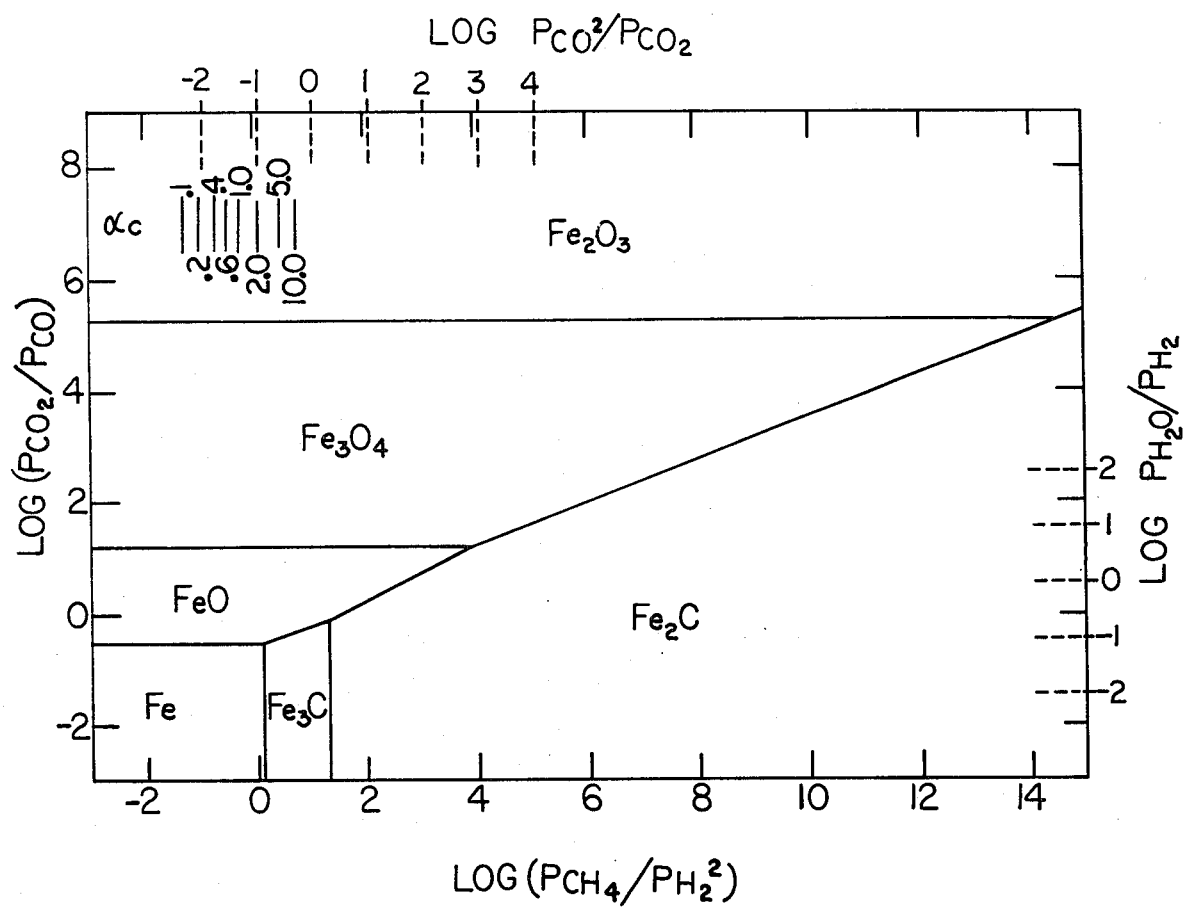
Figure 3:
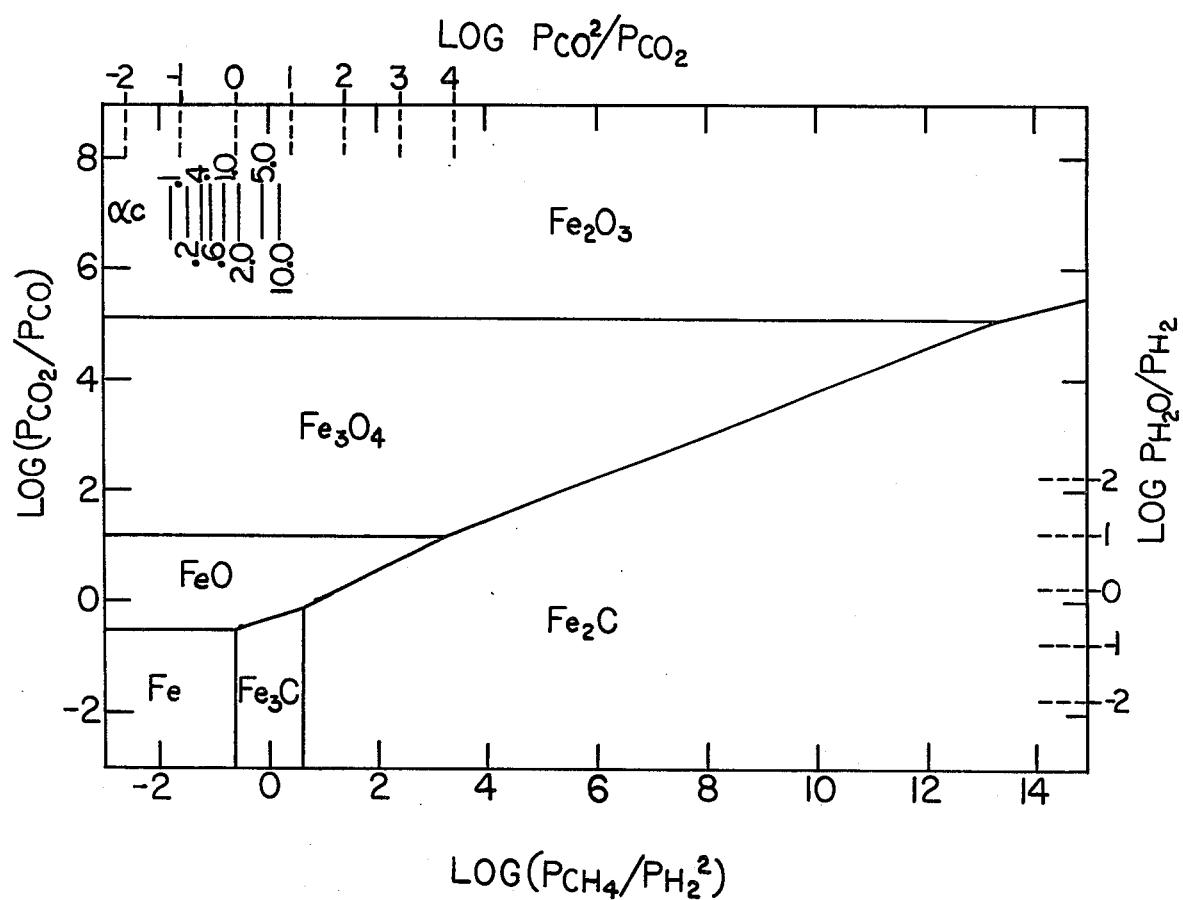

FIGS. 1, 2 and 3 are stability diagrams indicating the gas phase relationships between iron carbide and the hydrogen carbon-oxygen system at temperatures of 1160°, 1070° and 1250° F, respectively. The stability diagrams indicate the relationship between log plots of partial pressure ratios of the various gas components which are in equilibrium with iron carbide in the present process. These illustrate that definite amounts of methane will exist in the system in the presence of the iron carbide, and that the amount of methane present or produced can be controlled by controlling the other variables in the system. For example, the charts indicate the operative range of variables at specified temperatures for insuring that $Fe_3C$ is present in the fluid bed. They also show the effect of temperature on the production of methane and $Fe_3C$ when the other variables for insuring the presence of $Fe_3C$ in the fluid bed are maintained substantially constant.

A feasible temperature range for the process is about 600° F to about 1200° F, preferably about 600° F to about 950° F. Temperatures outside these ranges are not economically feasible. Atmospheric pressures can be used and are preferred, although slightly elevated pressures of up to about 10 atmospheres are also suitable. Higher pressures are uneconomical.

The iron to iron carbide ratio in the reaction area can vary between about 10 percent iron carbide to 96 percent or more iron carbide. Iron may be added in metallic form or supplied from various sources, including iron oxide. Some carbon dioxide can be used in the feed gas as a source of carbon. It is an advantage of the process that oxygen is removed from the process in the form of water which is easily recovered. If any methane is fed into the reactor, it is unreacted and recovered with the product gas.

A 50 percent mixture of methane with carbon monoxide and hydrogen gives a gas mixture of 600 Btu. As can be seen from the examples below, this intermediate fuel gas is easily produced by the process of the invention.

EXAMPLE 1

Using the stability diagrams, a computer program was constructed which gives the equilibrium gas composition expected for the process when various hydrogen and carbon bearing gases are contacted with iron-iron carbide mixtures at various temperatures. Table 1 below shows examples of results obtained from this computer program under varying conditions of inlet gas composition, temperature and pressure under which the process is performed within the favorable methane production gas ratios illustrated in FIGS. 1 – 3.

TABLE 7
Equilibrium Shift Calculations for $Fe_3C$ System

| Temp °F | Pressure Atm | Inlet Gas, Volume Percent | | | | | | Off-gas, Volume Percent | | | | | | Btu/scf Inlet Gas | Btu/scf Off Gas |
|---|---|---|---|---|---|---|---|---|---|---|---|---|---|---|---|
| | | $H_2$ | $H_2O$ | CO | $CO_2$ | $CH_4$ | $N_2$ | $H_2$ | $H_2O$ | CO | $CO_2$ | $CH_4$ | $N_2$ | | |
| Section 1 | | | | | | | | | | | | | | | |
| 750 | 1 | 48.0 | 2.0 | 39.0 | 5.0 | 1.0 | 5.0 | 4.6 | 9.7 | 1.7 | 38.0 | 37.5 | 8.6 | 292 | 434 |
| 840 | 1 | 48.0 | 2.0 | 39.0 | 5.0 | 1.0 | 5.0 | 8.0 | 9.0 | 4.5 | 35.6 | 34.7 | 8.3 | 292 | 422 |
| 930 | 1 | 48.0 | 2.0 | 39.0 | 5.0 | 1.0 | 5.0 | 13.0 | 8.5 | 9.7 | 30.9 | 30.0 | 7.8 | 292 | 405 |
| 1020 | 1 | 48.0 | 2.0 | 39.0 | 5.0 | 1.0 | 5.0 | 19.8 | 8.0 | 17.1 | 24.2 | 23.6 | 7.2 | 292 | 382 |
| 1110 | 1 | 48.0 | 2.0 | 39.0 | 5.0 | 1.0 | 5.0 | 27.9 | 7.1 | 25.2 | 17.0 | 16.3 | 6.5 | 292 | 356 |
| 1200 | 1 | 48.0 | 2.0 | 39.0 | 5.0 | 1.0 | 5.0 | 35.6 | 5.9 | 32.1 | 10.8 | 9.7 | 5.8 | 292 | 331 |
| 1290 | 1 | 48.0 | 2.0 | 39.0 | 5.0 | 1.0 | 5.0 | 41.6 | 4.6 | 36.8 | 6.7 | 4.9 | 5.4 | 292 | 312 |
| Section 2 | | | | | | | | | | | | | | | |
| 750 | 1 | 53.0 | 1.0 | 31.0 | 1.0 | 13.0 | 1.0 | 7.7 | 16.4 | 0.9 | 19.4 | 54.0 | 1.7 | 400 | 674 |
| 840 | 1 | 53.0 | 1.0 | 31.0 | 1.0 | 13.0 | 1.0 | 12.7 | 14.0 | 2.5 | 18.9 | 50.0 | 1.6 | 400 | 638 |
| 930 | 1 | 53.0 | 1.0 | 31.0 | 1.0 | 13.0 | 1.0 | 19.3 | 11.4 | 5.9 | 17.0 | 44.9 | 1.5 | 400 | 595 |
| Section 3 | | | | | | | | | | | | | | | |
| 930 | 1 | 48.0 | 2.0 | 39.0 | 5.0 | 1.0 | 5.0 | 13.0 | 8.5 | 9.7 | 30.9 | 30.0 | 7.8 | 292 | 405 |
| 930 | 5 | 48.0 | 2.0 | 39.0 | 5.0 | 1.0 | 5.0 | 6.3 | 10.0 | 4.6 | 35.4 | 35.3 | 8.4 | 292 | 429 |
| 930 | 10 | 48.0 | 2.0 | 39.0 | 5.0 | 1.0 | 5.0 | 4.6 | 10.4 | 3.3 | 36.5 | 36.7 | 8.5 | 292 | 435 |

The results recorded in section 1 of Table 1 show the theoretical change in composition resulting when a gas having a composition similar to commercially produced "blue water gas" is subjected to the computerized program.

The results in section 2 of the Table show the theoretical change in composition obtained when a gas having a composition similar to gas produced by the Lurgi oxygen-pressure gasification is subjected to the computerized process. The large increase in yields of methane within a well defined temperature range graphically illustrates the critical effect of temperature on the yield of methane.

The results in section 3 of the Table show the theoretical effect of pressure on the yield of methane when the computerized process is applied to the same gas used for the section 1 tests. Methane yield is increased from 30 volume percent to 36.7 volume percent by increasing the pressure from one to ten atmospheres. Increased pressures would probably show slight increase in methane production but such pressures become uneconomic.

EXAMPLE 2

In order to further illustrate the operativeness of the invention and to illustrate the correlation between the results obtained by the computer application of the process and actual operation of the process, bench scale tests were made of the process. The tests were run in accordance with previously described procedure. Adequate iron and iron carbide were present in the fluid bed to start the reaction. No further addition of these components was necessary. Results from actual tests are recorded in each section with results from the computerized test under identical conditions. The results are recorded in Table 2.

TABLE 2

Experimental Shift Data for Fe₃C System

| | Temp °F | Pressure Atm | Inlet Gas, Volume Percent | | | | | | Off-gas, Volume Percent | | | | | | Btu/scf Inlet Gas | Btu/scf Off-Gas |
|---|---|---|---|---|---|---|---|---|---|---|---|---|---|---|---|---|
| | | | $H_2$ | $H_2O$ | CO | $CO_2$ | $CH_4$ | $N_2$ | $H_2$ | $H_2O$ | CO | $CO_2$ | $CH_4$ | $N_2$ | | |
| *Section 1* | | | | | | | | | | | | | | | | |
| Actual | 1020 | 1 | 65.0 | 2.0 | 33.0 | 0 | 0 | 0 | 60.7 | 2.5 | 12.6 | 2.4 | 21.8 | 0 | 317 | 461 |
| Computer | 1020 | 1 | 65.0 | 2.0 | 33.0 | 0 | 0 | 0 | 38.8 | 1.7 | 10.5 | 17.2 | 31.8 | 0 | 317 | 481 |
| *Section 2* | | | | | | | | | | | | | | | | |
| Actual | 1020 | 1 | 22.0 | 1.7 | 17.7 | 13.3 | 7.8 | 37.5 | 30.2 | 1.1 | 13.0 | 4.8 | 12.5 | 38.4 | 207 | 264 |
| Computer | 1020 | 1 | 22.0 | 1.7 | 17.7 | 13.3 | 7.8 | 37.5 | 15.9 | 1.9 | 16.2 | 5.7 | 13.3 | 47.0 | 207 | 239 |

The results recorded in section 1 of Table 2 are from a test program using a 3:1 mixture of hydrogen to carbon monoxide as the inlet gas, this gas representing a gasification process working with oxygen. At 1020° F the actual test produced a gas with 21.8 percent methane and a Btu value of 461 as compared to the predicted values of 31.8 percent methane and 481 Btu's.

The results recorded in section 2 of Table 2 show the change in composition obtained by the process in a representative gas containing relatively large amounts of inert nitrogen, this gas representing a gasification process working with air. The actual test produced a gas with 12.5 percent methane and a Btu value of 264 as compared to a predicted methane content of 13.3 percent and a Btu value of 239. An increase in Btu value of over 30 percent was obtained in both instances.

The test results established the operativeness of the process for producing methane, and prove the validity of the stability diagrams of FIGS. 1-3 for use in selecting conditions for operative and feasible production of methane.

EXAMPLE 3

Various gases were fed at a rate of 200 cubic feet per minute to a two foot diameter fluidized-bed reactor containing sufficient iron and iron carbide to start the reaction. No further addition of these materials was necessary. The inlet gases consisted of hydrogen, carbon monoxide and carbon dioxide introduced in amounts conforming to favorable methane production ratios illustrated in FIGS. 1-3. A temperature of 930° F and atmospheric pressure were used for all the tests. The inlet gas had a composition of approximately 82 percent hydrogen, 8 percent carbon dioxide and 10 percent methane with a Btu value of about 370. The ratio of iron carbide to iron varied from a ratio of about 73/27 percent to 96/4 percent.

Analyses were made of the off-gas taken at half-hour intervals for a 12 hour period, the results of which are presented in Table 3.

TABLE 3

Pilot Plant Gas Composition Data
Reactor Products-Solid, Gas

| Time | Off Gas | | | | | | Ratio | | |
|---|---|---|---|---|---|---|---|---|---|
| | $H_2O$ | $CO_2$ | CO | $N_2$ | $H_2$ | $CH_4$ | CO/$CO_2$ | $H_2$/$H_2O$ | $H_2$/$CH_3$ |
| 2400 | 1.2 | 4.5 | 3.9 | 8 | 35 | 44 | 0.9 | 29.2 | 0.8 |
| 0030 | 1.2 | 4.5 | 3.9 | 8 | 33 | 44 | 0.9 | 27.5 | 0.8 |
| 0100 | 1.0 | 4.5 | 3.9 | 8 | 35 | 44 | 0.9 | 35.0 | 0.8 |
| 0130 | 1.0 | 4.8 | 4.2 | 8 | 35 | 43 | 0.9 | 35.0 | 0.8 |
| 0200 | 1.0 | 4.8 | 4.2 | 8 | 35 | 44 | 0.9 | 35.0 | 0.8 |
| 0230 | 1.0 | 4.8 | 4.2 | 8 | 35 | 44 | 0.9 | 35.0 | 0.8 |
| 0300 | 1.0 | 4.8 | 4.0 | 8 | 34 | 42 | 0.8 | 34.0 | 0.8 |
| 0330 | 1.0 | 4.8 | 4.2 | 8 | 34 | 43 | 0.9 | 34.0 | 0.8 |
| 0400 | 1.0 | 4.8 | 4.2 | 8 | 34 | 43 | 0.9 | 34.0 | 0.8 |
| 0430 | 1.0 | 5.5 | 4.2 | 8 | 35 | 43 | 0.8 | 35.0 | 0.8 |
| 0500 | 1.0 | 5.5 | 4.0 | 8 | 35 | 43 | 0.7 | 35.0 | 0.8 |
| 0530 | 1.0 | 6.7 | 4.8 | 8 | 35 | 40 | 0.7 | 35.0 | 0.9 |
| 0600 | 1.0 | 6.2 | 4.8 | 8 | 35 | 40 | 0.8 | 35.0 | 0.9 |
| 0630 | 1.0 | 6.2 | 4.8 | 8 | 35 | 41 | 0.8 | 35.0 | 0.9 |
| 0700 | 1.0 | 6.2 | 5.0 | 8 | 35 | 40 | 0.8 | 35.0 | 0.9 |
| 0730 | 1.0 | 6.7 | 5.1 | 8 | 35 | 40 | 0.8 | 35.0 | 0.9 |
| 0800 | 2.4 | 7.5 | 7.9 | 7 | 35 | 40 | 1.1 | 14.6 | 0.9 |
| 0830 | 2.4 | 7.75 | 8.25 | 6.5 | 35 | 39 | 1.1 | 14.6 | 0.9 |
| 0900 | 2.4 | 8.6 | 8.9 | 7 | 34 | 38.3 | 1.0 | 14.2 | 0.9 |
| 0930 | 2.4 | 5.3 | 6.6 | 7 | 38 | 40 | 1.3 | 15.8 | 1.0 |
| 1000 | 2.3 | 4.4 | 4.5 | 5.5 | 41 | 33.5 | 1.0 | 17.8 | 1.2 |
| 1030 | 2.3 | 3.6 | 4.5 | 5.5 | 40 | 40 | 1.3 | 17.4 | 1.0 |
| 1100 | 2.4 | 4.5 | 5.2 | 7 | 39 | 41.5 | 1.2 | 16.3 | 0.9 |
| 1130 | 2.3 | 4.8 | 6.5 | 7 | 37 | 41.5 | 1.4 | 16.1 | 0.9 |

The average methane content of the off-gas during the 12-hour period exceeded 40 percent and the off-gas had a Btu average value of about 560 as compared to the Btu value of only 370 for the inlet gas.

Again, the results of the table show the feasibility of the process for strongly enhancing the Btu value of a gas, including one containing methane. The results illustrate the feasible time period for the enhancement. Further, the results show that large amounts of methane are produced with large percentages of iron carbide to iron present in the fluid bed. For example, at 1000 the percentage of iron carbide to iron in the bed was about 96 percent. The results further establish the validity of the stability diagrams of FIGS. 1-3 for use in selecting favorable operating conditions for the process.

What is claimed is:

1. A process for converting a first gas mixture containing carbon monoxide and hydrogen into a second gas mixture having a substantially increased fuel value, comprising methane, in a single reaction zone which comprises:

(a) maintaining iron and $Fe_3C$ in a fluid bed;

(b) continuously introducing said first gas mixture into said fluid bed;

(c) maintaining a temperature of about 600° F – 1200° F and a pressure of about 1–10 atmospheres in said fluid bed so that some of the carbon monoxide is reduced to carbon, the iron is reacted with carbon to form $Fe_3C$, and the $Fe_3C$ is reacted with hydrogen to form methane and reform iron, and (d) continuously removing from said fluid bed as a product said second gas mixture of methane, carbon monoxide and hydrogen having an increased fuel value.

2. The process of claim 1 in which carbon dioxide is added to the first gas mixture as a source of carbon.

3. The process of claim 1 performed at a temperature between about 600° F and 950° F.

4. The process of claim 1 in which methane is separated from said second gas mixture and recovered as a product.

5. The process of claim 4 in which methane is separated from said second gas mixture and recovered as a product.

6. A process for making methane from a gas mixture of carbon monoxide and hydrogen in a single reaction zone which comprises:

(a) maintaining iron and $Fe_3C$ in a fluid bed;

(b) continuously introducing said gas mixture into said fluid bed;

(c) maintaining a temperature of about 600° F – 1200° F and a pressure of about 1–10 atmospheres in said fluid bed so that some of the carbon monoxide is reduced to carbon, the iron is reacted with carbon to form $Fe_3C$, and the $Fe_3C$ is reacted with hydrogen to form methane and reform iron, and (d) continuously recovering methane from the resulting gas mixture.

7. The process of claim 6 performed at a temperature beween about 600° F – 950° F.

* * * * *